(12) United States Patent
Nagata et al.

(10) Patent No.: US 7,907,995 B2
(45) Date of Patent: Mar. 15, 2011

(54) ELECTROCARDIOGRAPHY CHART APPARATUS AND METHOD THEREOF

(75) Inventors: Shinya Nagata, Kobe (JP); Ryuji Nagai, Takatsuki (JP); Kenji Kouchi, Toyonaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 859 days.

(21) Appl. No.: 10/506,434

(22) PCT Filed: Mar. 4, 2003

(86) PCT No.: PCT/JP03/02456
§ 371 (c)(1),
(2), (4) Date: Sep. 2, 2004

(87) PCT Pub. No.: WO03/073931
PCT Pub. Date: Sep. 12, 2003

(65) Prior Publication Data
US 2005/0182333 A1    Aug. 18, 2005

(30) Foreign Application Priority Data

Mar. 5, 2002 (JP) ................. 2002-058751
Jul. 5, 2002 (JP) ................. 2002-197298

(51) Int. Cl.
*A61B 5/044* (2006.01)
(52) U.S. Cl. .................................... 600/523
(58) Field of Classification Search ............. 600/509, 600/523, 407; 607/9
See application file for complete search history.

(56) References Cited

U.S. PATENT DOCUMENTS 3,983,867 A * 10/1976 Case .................. 600/522
4,214,590 A *  7/1980 Patnoi et al. ........... 600/523
4,794,934 A *  1/1989 Motoyama et al. ....... 600/547

(Continued)

FOREIGN PATENT DOCUMENTS

JP        53-133991        11/1978

(Continued)

OTHER PUBLICATIONS

Dale Dubin, Rapid Interpretation of EKGs, 2000 Cover Inc., 6th edition, pp. 53,209,236.*

(Continued)

*Primary Examiner* — Carl H Layno
*Assistant Examiner* — Luther G Behringer
(74) *Attorney, Agent, or Firm* — Jason H. Vick; Sheridan Ross P.C.

(57) ABSTRACT

An electrocardiogram (ECG) chart device and method capable of easily assisting with the diagnosis of heart disease. Hexagonal radar charts displayed on a screen act as indicators of feature values corresponding to data obtained from each of 12 electrode leads and correlated with the related portions of the heart. For example, a (V1, V2) lead is an indicator of a right ventricle. Each of the radar charts is schematically arranged to correspond with the related portion of the heart. Each vertex of the hexagonal radar charts acts as an indicator of the recognized value. More specifically, each vertex of the radar chart is based on a value obtained by extracting a waveform critical point, a waveform start point, a waveform end point, or the like, of constituent elements of the ECG waveform as the P wave, the Q wave, the R wave, the S wave, the ST segment, the T wave, or the like. Therefore, a user of the ECG radar chart device can intuitively and easily carry out interpretation of ECG data.

8 Claims, 16 Drawing Sheets

U.S. PATENT DOCUMENTS

| | | | |
|---|---|---|---|
| 4,898,181 A | 2/1990 | Kessler | |
| 5,020,540 A * | 6/1991 | Chamoun | 600/509 |
| 5,109,862 A | 5/1992 | Kelen et al. | |
| 5,410,473 A | 4/1995 | Kaneko et al. | |
| 5,611,034 A | 3/1997 | Makita | |
| 5,634,469 A | 6/1997 | Bruder et al. | |
| 5,694,945 A * | 12/1997 | Ben-Haim | 600/407 |
| 5,803,084 A * | 9/1998 | Olson | 600/512 |
| 5,891,045 A | 4/1999 | Albrecht et al. | |
| 6,047,206 A | 4/2000 | Albrecht et al. | |
| 6,112,119 A * | 8/2000 | Schuelke et al. | 607/9 |
| 6,230,048 B1 * | 5/2001 | Selvester et al. | 600/523 |
| 6,322,516 B1 | 11/2001 | Masuda et al. | |
| 6,574,503 B2 | 6/2003 | Ferek-Petric | |
| 6,702,754 B2 * | 3/2004 | Ogura et al. | 600/500 |
| 6,725,088 B2 * | 4/2004 | Baba et al. | 600/547 |
| 6,748,274 B2 | 6/2004 | Levine et al. | |
| 6,778,852 B2 | 8/2004 | Galen et al. | |
| 6,856,832 B1 * | 2/2005 | Matsumura et al. | 600/523 |
| 2001/0005830 A1 | 6/2001 | Kuroyanagi | |
| 2001/0053883 A1 | 12/2001 | Yoshimura et al. | |
| 2002/0016551 A1 | 2/2002 | Selvester et al. | |
| 2003/0097056 A1 | 5/2003 | Suzuki et al. | |
| 2003/0135097 A1 | 7/2003 | Wiederhold et al. | |
| 2003/0200114 A1 | 10/2003 | Ogino et al. | |
| 2003/0208128 A1 * | 11/2003 | Hamilton et al. | 600/509 |

FOREIGN PATENT DOCUMENTS

| | | | |
|---|---|---|---|
| JP | 61-51801 | | 4/1986 |
| JP | 62-152434 | | 7/1987 |
| JP | S62-152434 | | 7/1987 |
| JP | 62-217936 | | 9/1987 |
| JP | 62-231622 | | 10/1987 |
| JP | 63-150053 | | 6/1988 |
| JP | 5-176906 | | 7/1993 |
| JP | 6-181898 | | 7/1994 |
| JP | 6-181899 | | 7/1994 |
| JP | H6-205751 | * | 7/1994 |
| JP | 6-261871 | | 9/1994 |
| JP | 7-67843 | | 3/1995 |
| JP | 8-280644 | | 10/1996 |
| JP | 11-318841 | | 11/1999 |
| JP | 2001-37729 | | 2/2001 |

OTHER PUBLICATIONS

Chinese Official Action (including translation) mailed Oct. 13, 2006 for corresponding Chinese Patent Application.
International Preliminary Examination Report for PCT/JP2003/002456.
Supplementary European Search Report for European Application No. 03743569.0, dated Apr. 28, 2009.
International Preliminary Examination Report for PCT/JP2003/002456 (English Translation).
U.S. Appl. No. 11/862,641, filed Sep. 27, 2007, Nagata et al.
Official Action for European Application No. 03743569.0-1265 dated Sep. 2, 2009.
Official Action for European Patent Application No. 03743569.0, dated Apr. 7, 2010.
International Search Report (including translation) for International (PCT) Application No. PCT/JP2003/002456, mailed May 27, 2003.
Official Action for U.S. Appl. No. 11/862,641, mailed May 13, 2010.
Blattner et al., "Using Excel 2000," May 1999, 4 pages.

* cited by examiner

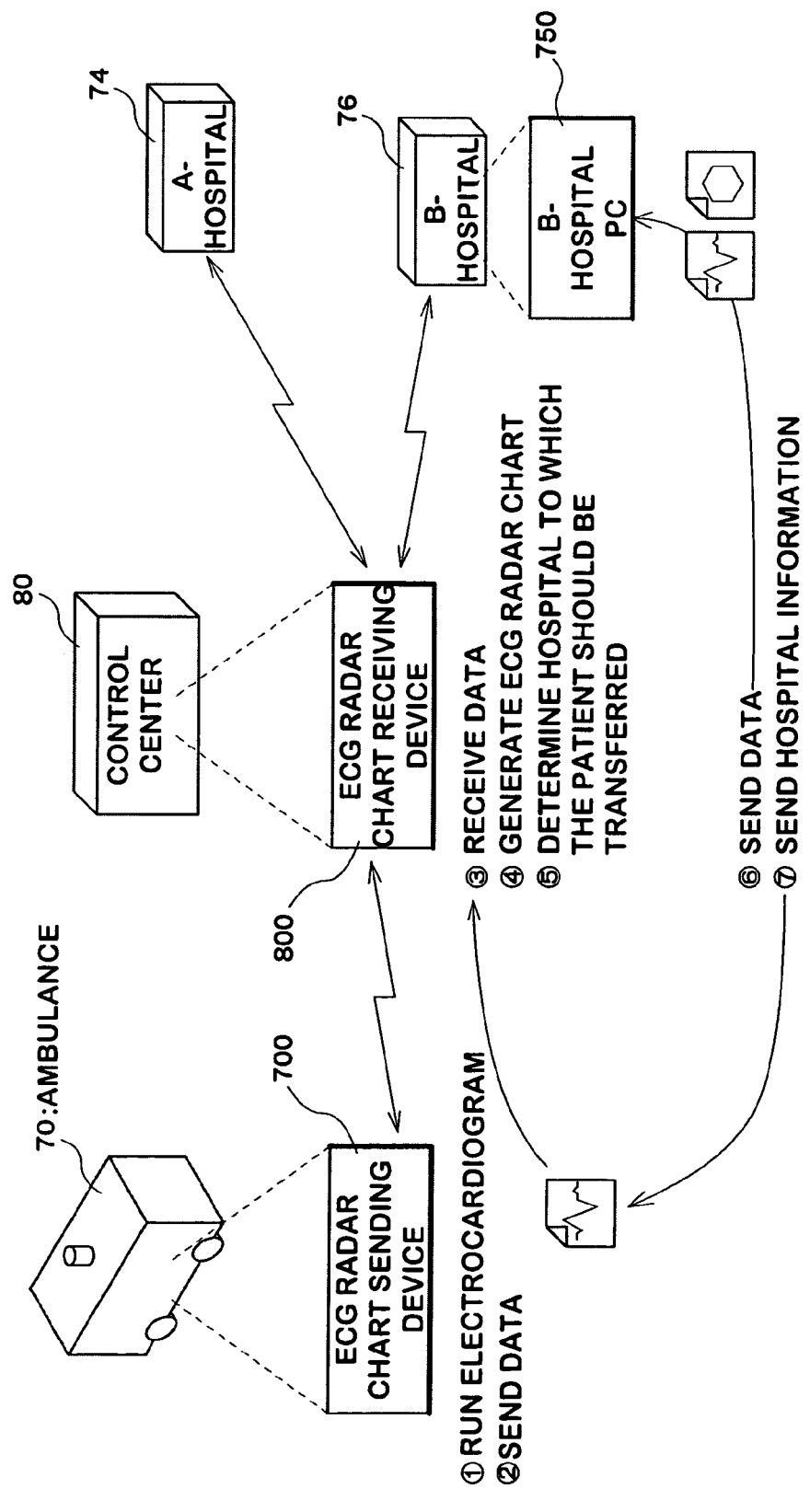

FIG.16A

| Data No. | LEAD I (mv) | LEAD V1 (mv) | ... |
|---|---|---|---|
| 1501 | 0.01 | 0.03 | ... |
| 1502 | 0.01 | 0.03 | ... |
| 1503 | 0.00 | 0.02 | ... |
| 1504 | -0.01 | 0.02 | ... |
| 1505 | -0.02 | 0.02 | ... |
| 1506 | -0.03 | 0.01 | ... |
| --- | --- | --- | --- |

FIG.16B

| HB No. | ST (mv) | RR (sec) | ... |
|---|---|---|---|
| 011 | 0.01 | 0.66 | ... |
| 012 | 0.05 | 0.68 | ... |
| 013 | -0.01 | 0.80 | ... |
| 014 | 0.03 | 0.72 | ... |
| 015 | 1.24 | 0.62 | ... |
| 016 | 0.09 | 0.64 | ... |
| --- | --- | --- | --- |

ELECTROCARDIOGRAPHY CHART APPARATUS AND METHOD THEREOF

CROSS-REFERENCE TO RELATED APPLICATIONS

The present application claims the benefit of patent application number 2002-058751, filed in Japan on Mar. 5, 2002, and patent application number 2002-197298, filed in Japan on Jul. 5, 2002, the subject matters of which are hereby incorporated herein by reference.

BACKGROUND OF THE INVENTION

1. Field of the Invention

The present invention relates to a device and a method for displaying an electrocardiogram with certain display styles and more particularly to a display style capable of aiding with electrocardiogram interpretation.

2. Description of the Related Art

Several display techniques that improve the visualization of electrocardiogram ("ECG" as an abbreviation) waves have been developed in order to aid in detection of heart disease. An example of such a technique includes the bar graph display technique for displaying movement of the feature points of an ECG in a bar graph form. More specifically, Japanese Patent Laid-Open No. Hei 6-181899 discloses a display technique for displaying movement of the ST level on a 12-lead ECG in bar graph form (refer to FIG. 3 etc.). By "12-lead ECG" is meant 12 ECG measurements made by attaching from several to a dozen or so electrodes to a living body.

Since the above-mentioned technologies utilize only specific feature points, the technologies can help in discriminating from among specific types of heart diseases that affect the trends of the feature point. However, in emergency medical activities, including medical treatment at hospitals, technologies that can help in discrimination from among greater varieties of heart disease are required in order to determine appropriate hospitals or services promptly to which the patients should be transferred.

SUMMARY OF THE INVENTION

In one aspect, the invention provides a device and a method that are capable of providing aid to ease the means by which discrimination of a disease from among greater varieties of heart disease is carried out. The invention includes the following:

(1) An ECG chart data-generating device in accordance with the present invention generates chart data to be used to display charts based on measured ECG data. The ECG chart data-generating device includes means for generating feature value data indicating an ECG feature value and means for generating chart data based on the feature value data, wherein the chart data is to be displayed as a chart that relates the feature value to each portion of the heart.

The user, utilizing the chart displayed by the ECG chart data-generating device, can understand the feature values in connection with the related portion of the heart. Therefore, the user can promptly and easily carry out an assessment of heart diseases in connection with the corresponding portion of the heart.

(5) The chart data in accordance with the present invention is to be used to display a chart that arranges each feature value at the corresponding portion of the heart. The user, utilizing the chart displayed by the ECG chart data-generating device, can visually and intuitively understand the feature values in connection with the related portion of the heart. Therefore, the user can promptly and easily carry out an assessment of heart diseases in connection with the corresponding portion of the heart.

(6) The device in accordance with the present invention, further includes the ability to vary the display style of the feature value when the feature value is in an abnormal range.

The user, who utilizes the chart, can visually and intuitively understand that the feature value is in the abnormal range by checking the display style varied by the display controlling means. The user can also discern the portion of the heart that relates to the feature value in the abnormal range. Therefore, the user can promptly and easily carry out ECG interpretation in connection with specific heart diseases.

(8) The device in accordance with the present invention includes the ability for the display controlling means or means for displaying an abnormal value is to hold the display of the feature value constant even when the feature value varies within a normal range.

The display controlling means holds display of the feature value constant when the feature value varies within a normal range, while the display controlling means varies the display style of the feature value when the feature value is in an abnormal range. Therefore, the device can draw the user's attention to the display when the feature value is in an abnormal range.

(9) The device in accordance with the present invention further includes the ability for the chart data to be used to display a chart that relates the feature value to each portion of the heart including at least the left portion of the heart, the right portion of the heart, the bottom portion of the heart, the front portion of the heart, or the inner portion of the heart.

The user, utilizing the chart displayed by the ECG chart data-generating device, can visually and intuitively understand the feature values in connection with each portion of the heart including the left portion of the heart, the right portion of the heart, the bottom portion of the heart, the front portion of the heart, or the inner portion of the heart.

(10) The device in accordance with the present invention further includes the ability of feature value data to be based on the constituent elements of an ECG, including at least a P wave, a Q wave, an R wave, a S wave, a ST segment, or a T wave.

The user, utilizing the chart displayed by the ECG chart data-generating device, can visually and intuitively understand the feature values that are based on the constituent elements of an ECG including the P wave, the Q wave, the R wave, the S wave, the ST segment, or the T wave in connection with the related portion of the heart.

(11) The device in accordance with the present invention further includes the capability that the chart data is to be used to display the feature value in a radar chart form.

The user, utilizing the radar chart displayed by the ECG chart data-generating device, can collectively understand one or more of two feature values that are based on the corresponding constituent elements of the ECG, including the P wave, the Q wave, the R wave, the S wave, the ST segment, or the T wave, at the same time. Therefore, the user can promptly and intuitively carry out the assessment of heart diseases in connection with the related portion of the heart.

(12) The device in accordance with the present invention further includes the ability of the chart data is to be used to display the feature value on a heart image.

The user can visually and intuitively understand the feature values in connection with the heart image.

(13) An ECG display device in accordance with the present invention for displaying measured ECG data includes means for obtaining feature value data indicating an ECG feature value and means for displaying the feature value on a heart image.

The user can visually and intuitively understand the feature value data in connection with the heart image.

The term "feature value" in the present invention includes information such as an ECG waveform critical point value, a waveform start point value, a waveform end point value, a waveform segment point value, an amplitude value, a wave number value, a wavelength value, or information derived from those values (e.g. an interval value). In other words, the term "feature value" includes an identified value extracted from an ECG waveform, or information derived from the identified value.

The term "radar chart" in the present invention corresponds to a graph on which displayed points are displayed in a spider web format, and includes a polygonal-shaped display, such as a hexagon or pentagon, on which each displayed point is placed at a vertex of the polygonal shape.

The term "chart display" in the present invention includes displayed points or displayed values in certain forms such as a listing, a diagram, a graph, a meter, or gage form. More specifically, the term "chart display" includes a bar graph (refer to FIG. 7A), a two dimensional graph, a three dimensional graph (refer to FIG. 7B), or a combination of diagram and a displayed value listing (refer to FIG. 7C), as well as the radar chart display (refer to FIG. 2, FIG. 5, etc.).

The term "heart image" in the present invention includes a heart display in general. Examples of the term "heart image" include a heart displayed in freeze-frame picture or moving picture form, a deformed heart picture designed (or modified) by use of graphics software (e.g. a heart diagram or heart sketch), an animated heart, or a computer-generated heart image designed by use of computer graphics (CG) (e.g. a three dimensional stereograph heart image).

The features of the present invention can be described broadly as set forth above. The structures and characteristics of the present invention will be apparent from the following detailed description of the invention together with those features, effects, and drawings.

BRIEF DESCRIPTION OF THE DRAWINGS

FIG. 8 illustrates an ECG radar chart system as another embodiment.

FIG. 16A illustrates a diagram of stored ECG data.

FIG. 16B illustrates a diagram of stored identified value data.

DESCRIPTION OF THE PREFERRED EMBODIMENTS

Figure 1:
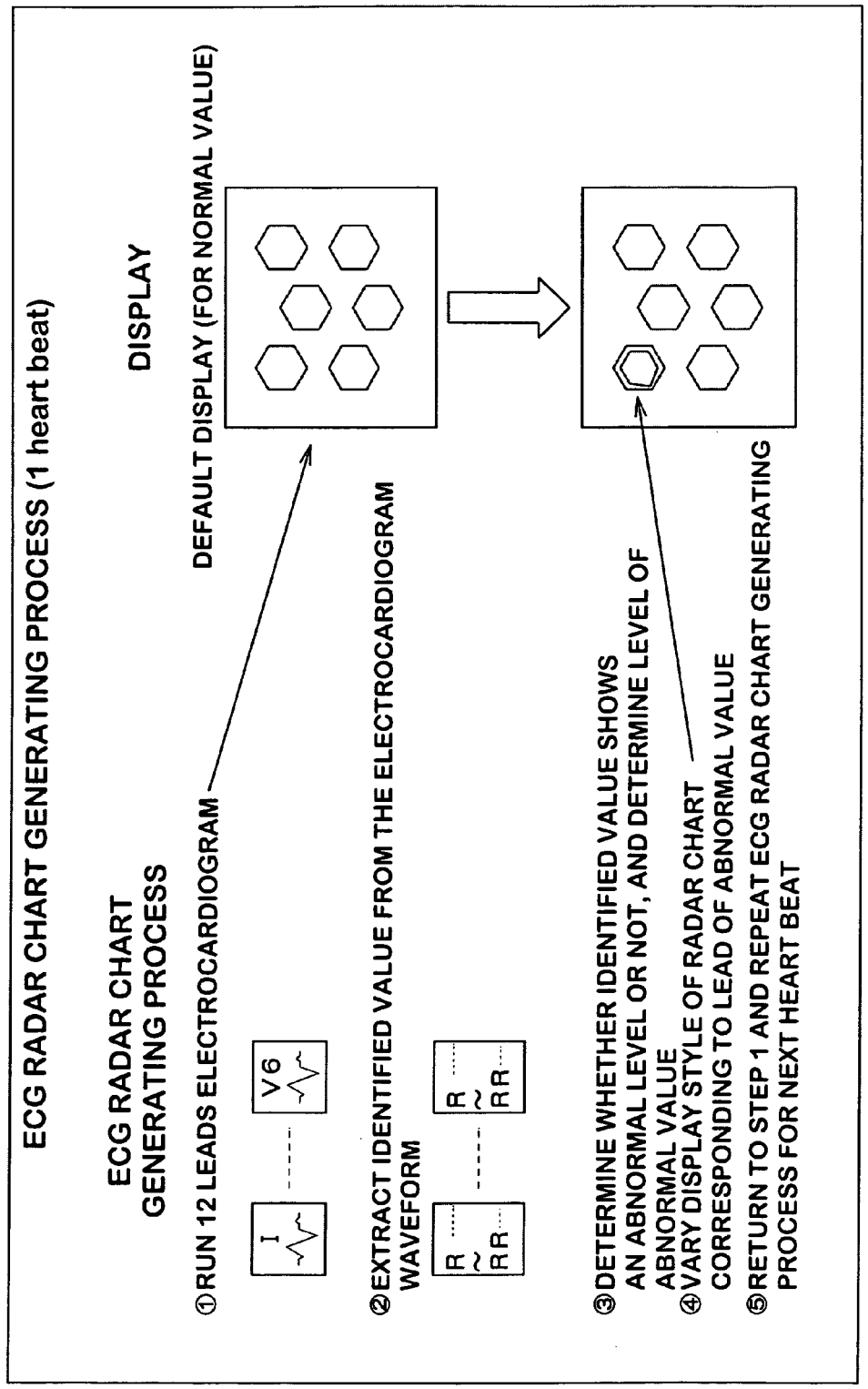
FIG. 1 illustrates a processing overview of an ECG radar chart device according to an embodiment of the present invention.

Embodiments according to the ECG chart device of the present invention will be described below. The "ECG chart device" corresponds to a device that has the functions of the "ECG chart data-generating device" and "ECG chart-display device." The following illustrates an ECG radar chart display processing based on the patient ECG data. According to the following embodiments, the user of the device can intuitively and easily carry out ECG interpretation in connection with specific heart diseases.

An overview of the embodiments, hardware configurations of devices, embodiments and structures corresponding to the terms in claims, and details of embodiments will be described below.

TABLE OF CONTENTS FOR THE EMBODIMENTS

1. An overview of the embodiments
2. Devices
3. Embodiments
4. ECG radar chart generation processing
5. Advantages of the embodiments
6. Other embodiments 1. An Overview of the Embodiments Embodiments of the present invention will be described below together with the accompanying drawings. The ECG radar chart device 100, as the ECG chart device in accordance with the present invention, runs an ECG on the patient and displays the ECG in a radar chart form. The device is suitable for use in emergency medical arenas such as in-ambulances or in-hospitals. The ECG is obtained by measuring electrical potential difference on the heart between two points on the patient's body. Therefore, the terms "ECG measurement" etc. used herein include the operations of measuring the heart's electrical potential etc.

2. Devices

Figure 3:
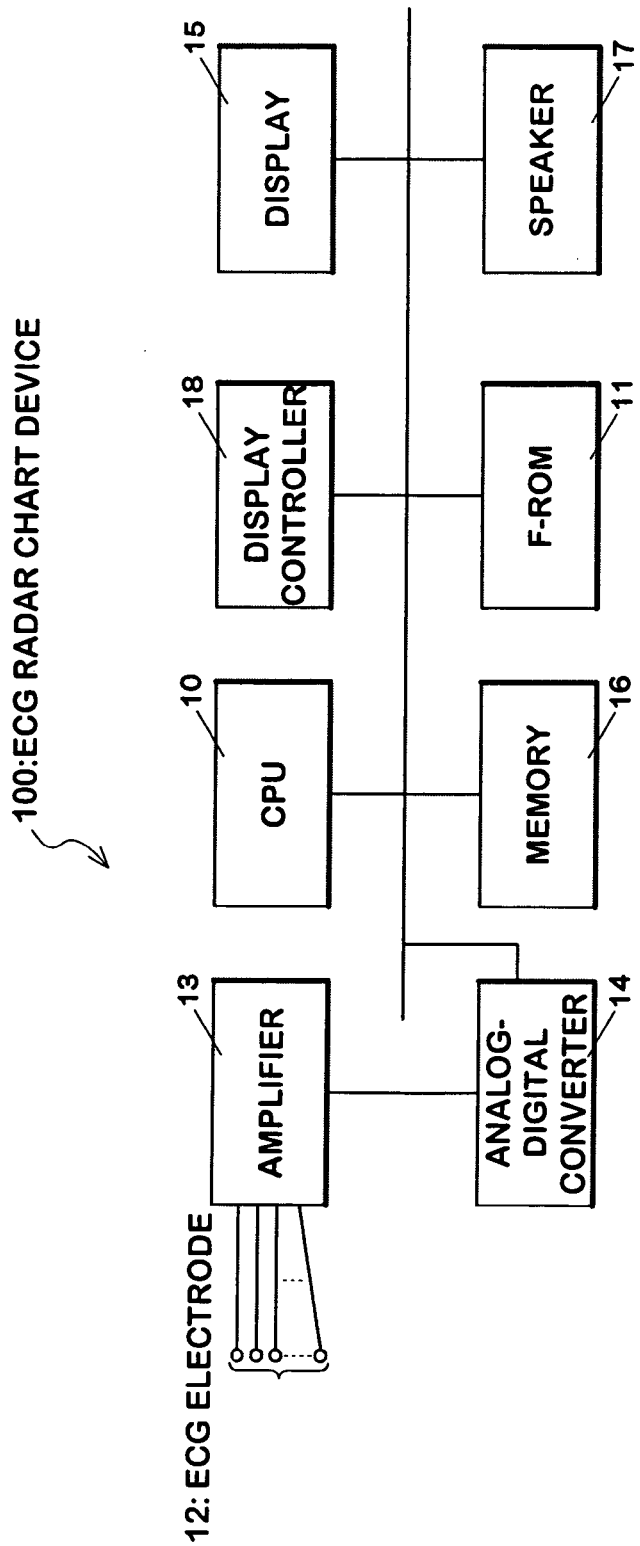
FIG. 3 illustrates a hardware configuration example for the ECG radar chart device.

FIG. 3 illustrates a hardware configuration example of the ECG radar chart device 100 by use of a central processing unit (CPU). The ECG radar chart device 100 includes ECG electrodes 12, amplifier 13, analog-digital converter 14, CPU 10, Flash-ROM 11 (which corresponds to a rewritable read-only memory device from which recorded data can be electrically erased (e.g. the flash-memory), and will be described as "F-ROM 11"), memory 16, display controller 18, display 15, and speaker 17.

The ECG electrodes 12 are used for measuring a patient's heart's electrical current. The amplifier 13 amplifies the heart's electrical current obtained through ECG electrodes 12. The CPU 10 controls operations of the ECG radar chart device 100, executes a process that converts data obtained from the heart's electrical signals to ECG data for displaying an ECG, and executes a process that displays an ECG radar chart. The F-ROM 11 stores a computer program for controlling the ECG radar chart device 100. The memory 16 acts as a storage area for data processing performed by the CPU 10. The display controller 18 controls the screen of display 15 in accordance with user operation.

In the embodiments, examples of operating systems for the ECG radar chart device 100 are Microsoft's Windows™ XP, NT, 2000, 98SE, ME, or CE. In alternative embodiments, the functions of the ECG radar chart device 100 are accomplished with hardware logic (not shown) without the use of a CPU. The hardware configuration or CPU configuration can be modified by well-known techniques by those skilled in the art.

3. Embodiments

The device performs the functions of an "ECG chart data-generating device" and "ECG chart-display device" corresponding to the ECG radar chart device 100 illustrated in FIG. 3. The "ECG data" correspond to the data for displaying an ECG, which are obtained by the CPU 10 of the ECG radar chart device 100 at step 403 in FIG. 4. The "feature value" corresponds to the identified value extracted from the ECG waveform by the CPU 10 at step 405 in FIG. 4. The "feature value data" correspond to data used for indicating the identified values (i.e. identified value data). The "feature value data-generating means" corresponds to the CPU 10 executing the process of step 405. The "display controlling means" corresponds to the CPU 10 executing the process of step 425 in FIG. 4.

Figure 2:
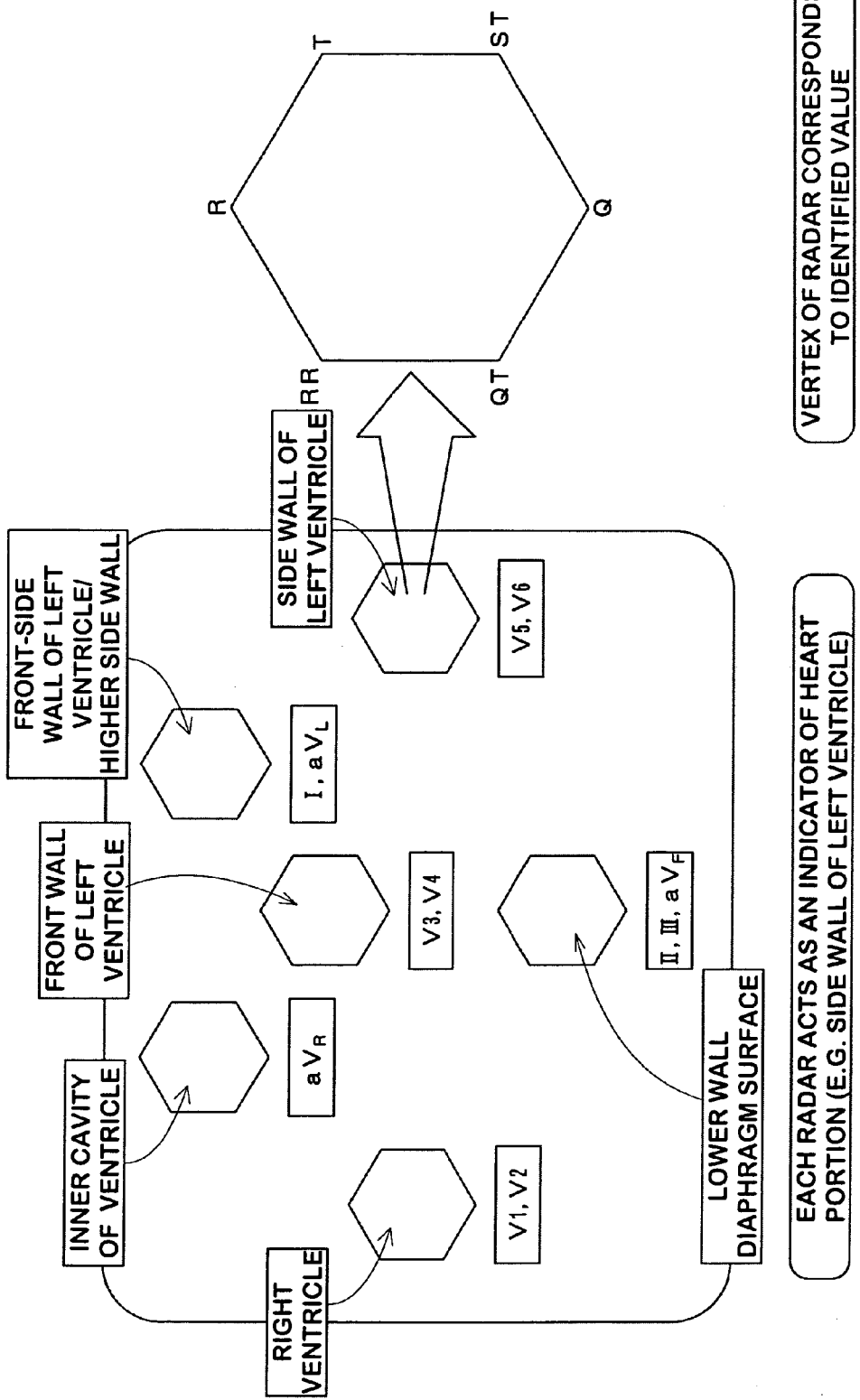
FIG. 2 illustrates an overview of an ECG radar chart screen.
Figure 5:
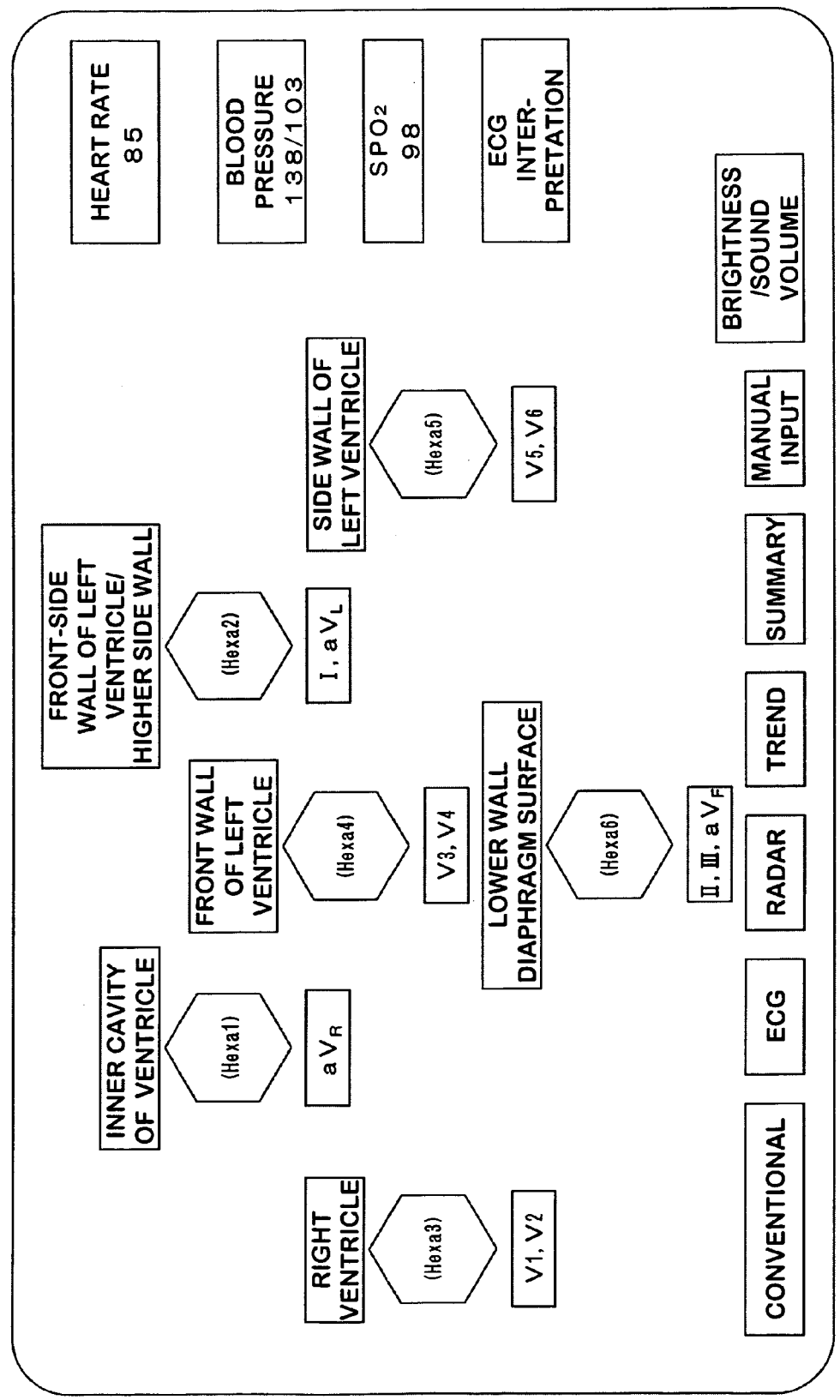
FIG. 5 illustrates an example of an ECG radar chart screen displaying values determined normal.

The "left portion of the heart" as the "portion of the heart" corresponds to the front-side wall of left ventricle, the higher side wall and/or the side wall of left ventricle as illustrated in FIG. 2 and FIG. 5, etc. The "right portion of the heart" corresponds to the right ventricle. The "bottom portion of the heart" corresponds to the lower wall diaphragm surface. The "front portion of the heart" corresponds to the front wall of left ventricle. The "inner portion of the heart" corresponds to the inner cavity of ventricle.

Figure 4:
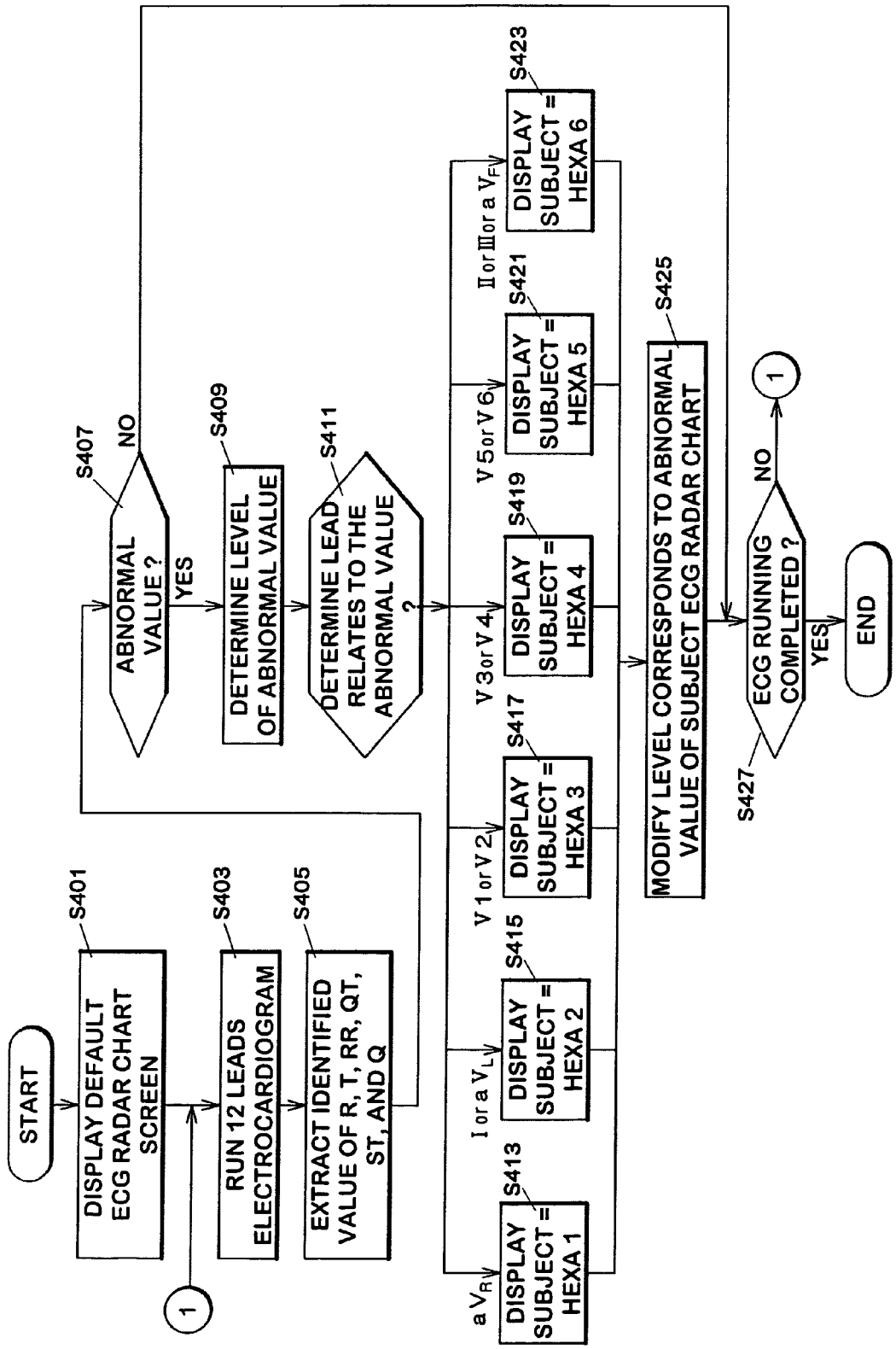
FIG. 4 illustrates a program flowchart for the ECG radar chart generating process of the ECG radar chart device.
Figure 6:
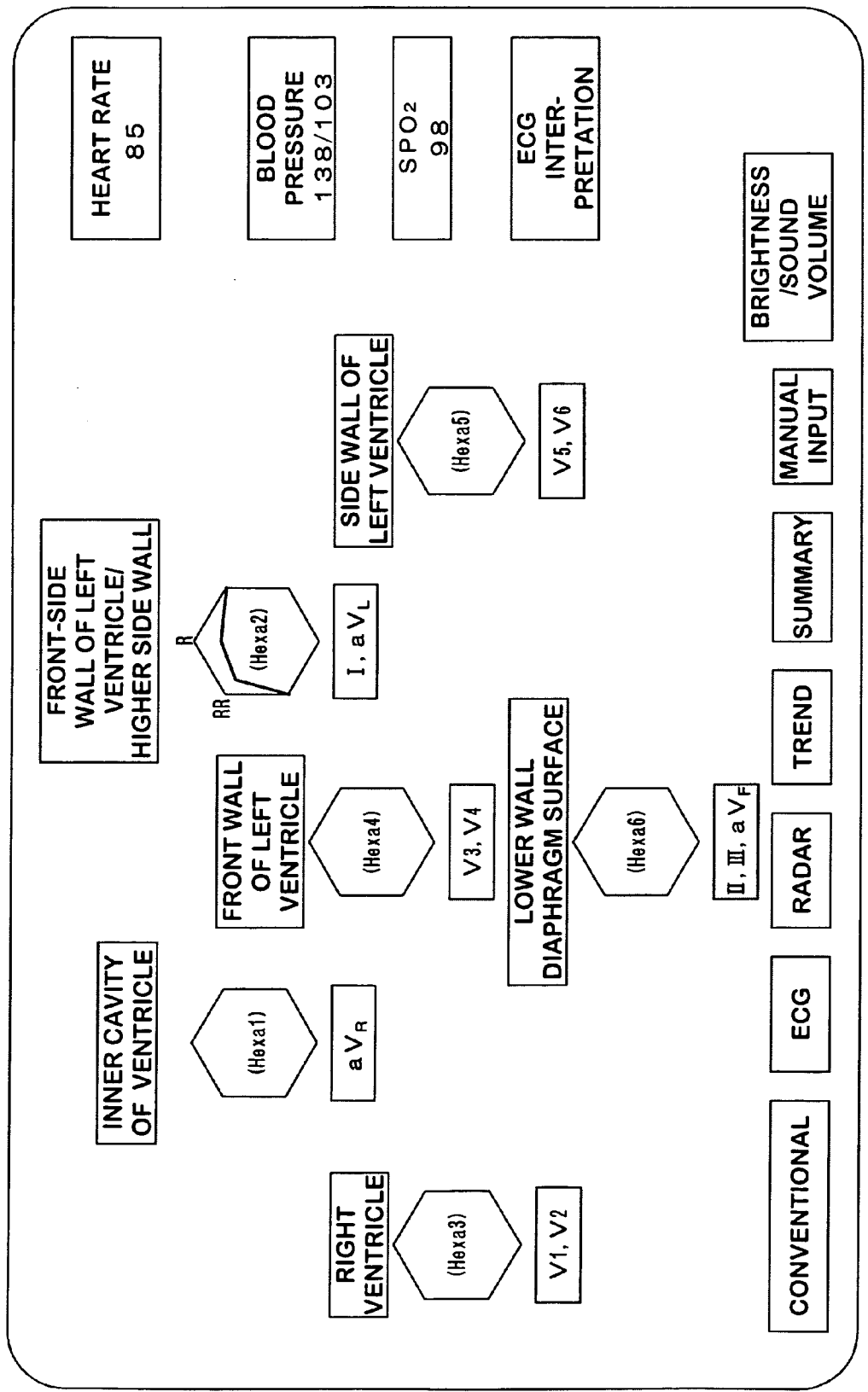
FIG. 6 illustrates an example of an ECG radar chart screen displaying a value determined abnormal.

The "chart data" correspond to data used for displaying the identified values in a radar chart form, as illustrated in FIG. 5 and FIG. 6, and the values are extracted by the CPU 10 as depicted at step 405 in FIG. 4. The "chart data-generating means" corresponds to the CPU 10 executing the process of step 411, 413, 415, 417, 419, 421, 423, or 425 in FIG. 4.

4. ECG Radar Chart Generation Processing

In this embodiment, as an example of the present invention, the CPU 10 of the ECG radar chart device 100 displays an ECG radar chart based on an ECG obtained from a patient. As an example, ECG radar chart generating process is executed once every heart beat. The sampling frequency for the ECG data is 125, 250, 500, 1000 Hz, or the like. In alternative embodiments, the timing for the ECG radar chart generating process can be modified by a well-known technique by those skilled in the art, such as at an every specific heart beat(s) other than the above-mentioned once every heart beat, or at other specified time periods. An overview of the ECG radar chart generating process and the process flowchart will be described below together with FIG. 1 etc. and FIG. 4, respectively.

4-1. An Overview of ECG Radar Chart Generation Processing

FIG. 1 illustrates an overview of the ECG radar chart generating process executed by the CPU 10 of ECG radar chart device 100. The CPU 10 runs 12-lead ECG on a patient (step 1). At this step, a default screen (i.e. screen for normal values) is displayed. An overview of the screen contents will follow. The CPU 10 extracts identified values (which are based on P wave, Q wave, R wave, S wave, ST segment, or T wave) from the ECG waveform (step 2). The CPU 10 determines for every identified value whether the identified value shows an abnormal level or not, and, determines the extent of the abnormality (step 3). If an abnormal value is present, the CPU 10 varies the display style of the radar chart (i.e. level of the radar) corresponding to the lead from which the abnormal value was obtained, and displays the radar chart as varied on the screen (step 4). The above-mentioned process is executed once every heart beat. At the next heart beat, the CPU 10 returns to step 1 and repeats the ECG radar chart generation process (step 5). The above-mentioned is an overview of the ECG radar chart generation process.

4-2. An Overview of the ECG Radar Chart Screen

FIG. 2 illustrates an overview of the ECG radar chart screen. As illustrated in FIG. 2, each hexagonal radar chart acts as an indicator for a portion of the heart corresponding to one or more of the 12 leads. More specifically, the (I, aVL) radar chart acts as an indicator for front-side wall of left ventricle and higher side wall. The (V3, V4) radar chart acts as an indicator for front wall of left ventricle. The (V5, V6) radar chart acts as an indicator for side wall of left ventricle. The (II, III, aVF) radar chart acts as an indicator for whole of lower heart portion (e.g. lower wall diaphragm surface). The (V1, V2) radar chart acts as an indicator for right ventricle. The (aVR) radar chart acts as an indicator for inner cavity of ventricle. Furthermore, each radar chart is placed at the corresponding portion of the heart on the schematic layout as illustrated in FIG. 2. The classification as "12-lead ECG" according to each portion of the heart as mentioned above can be modified by well-known techniques by those skilled in the art. Also, the layout for the radar charts according to the corresponding heart portion can be modified by well-known techniques by those skilled in the art.

As illustrated in FIG. 2, each vertex of a hexagonal radar chart acts an indicator for the identified value. More specifically, each point on the radar chart is adjusted on the basis of the value determined from a critical point, a start point, an end point, or etc., of the constituent element of the ECG waveform such as the P wave, the Q wave, the R wave, the S wave, the ST segment, or the T wave. In the embodiment, the values are six recognized values such as the R value (i.e. R potential or R wave height), the T value (i.e. T potential or T wave height), the Q value (i.e. Q potential or Q wave height), the ST value (i.e. ST level), the QT value (i.e. QT interval), and the RR value (i.e. RR interval).

While some radar charts correspond to one lead, other radar charts correspond to several leads, as illustrated in FIG. 2. For a radar chart corresponding to several leads, if at least one value is identified as abnormal, a screen for the abnormal value reflects the identified value. In addition, if several values are identified as abnormal, a screen for the abnormal values reflects the maximum or average of the identified values.

As mentioned above, the ECG radar chart device 100 displays the ECG radar chart based on the patient's ECG data. Therefore, the user of the device can intuitively and easily carry out ECG interpretation.

4-3. ECG Radar Chart Generation Processing

The program flowchart for the ECG radar chart generation process will be described below together with FIG. 4. FIG. 4 illustrates the program flowchart to be executed once every heart beat. Therefore, the program execution in accordance with the flowchart illustrated in FIG. 4 will be repeated once every heart beat during the patient's ECG measurement.

Figure 11:
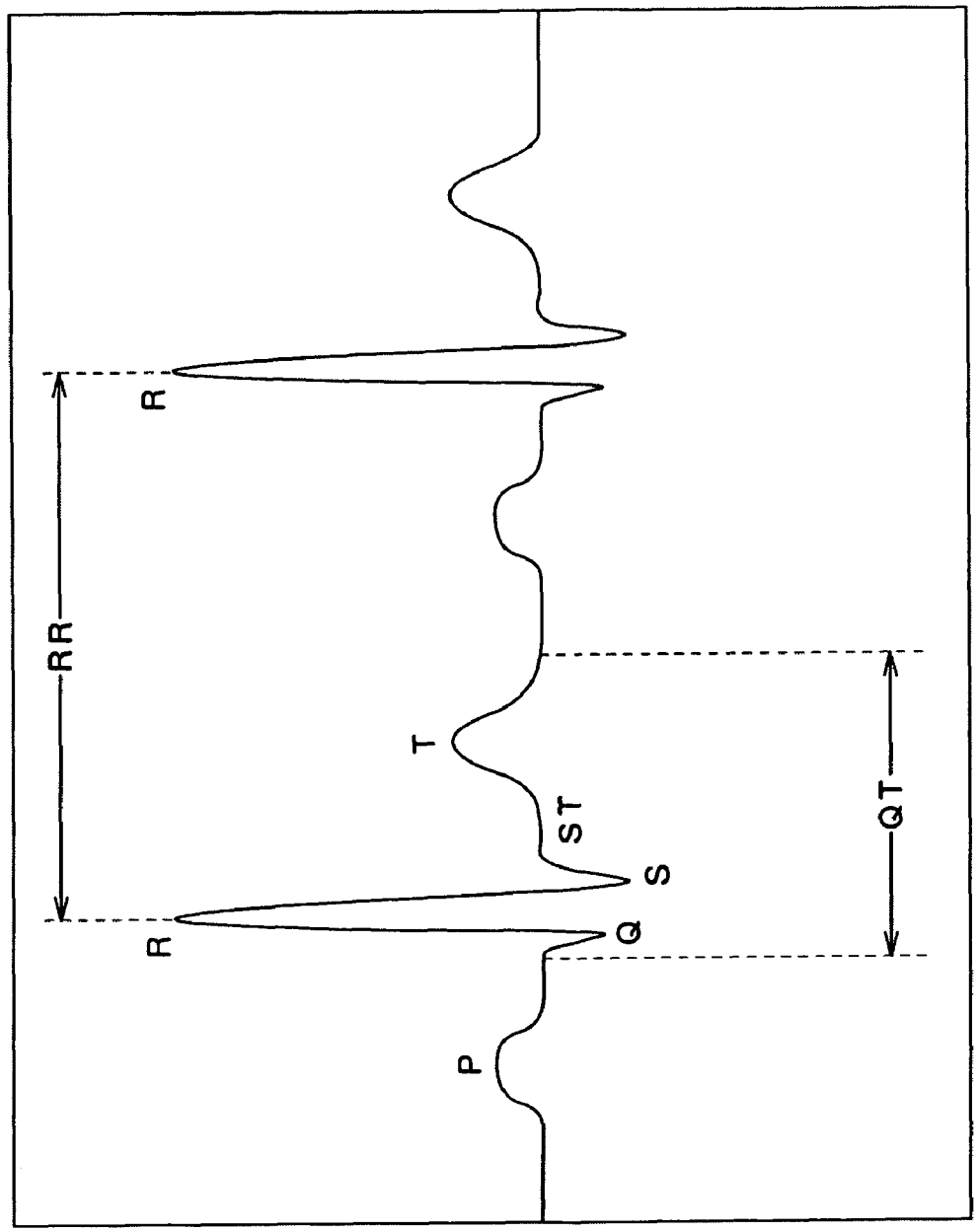
FIG. 11 illustrates an example of an ECG utilized by the CPU of the ECG radar chart device to obtain identified values.

FIG. 11 illustrates an example of an ECG utilized by the CPU of the ECG radar chart device to obtain an identified value. For example, the CPU identifies one heart beat by identifying (or extracting) all or some of the following: P value (i.e. P potential or P wave height), Q value (i.e. Q potential or Q wave height), R value (i.e. R potential or R wave height), S value (i.e. S potential or S wave height), T value (i.e. T potential or T wave height), ST value (i.e. ST level), QT value (i.e. QT interval), or RR value (i.e. RR interval) as identified value data (or feature value data) from the ECG data.

At the start of the ECG radar chart generation process, the CPU 10 of the ECG radar chart device 100 displays a default ECG radar chart screen on the display 15 (step 401 in FIG. 4).

Figure 12:
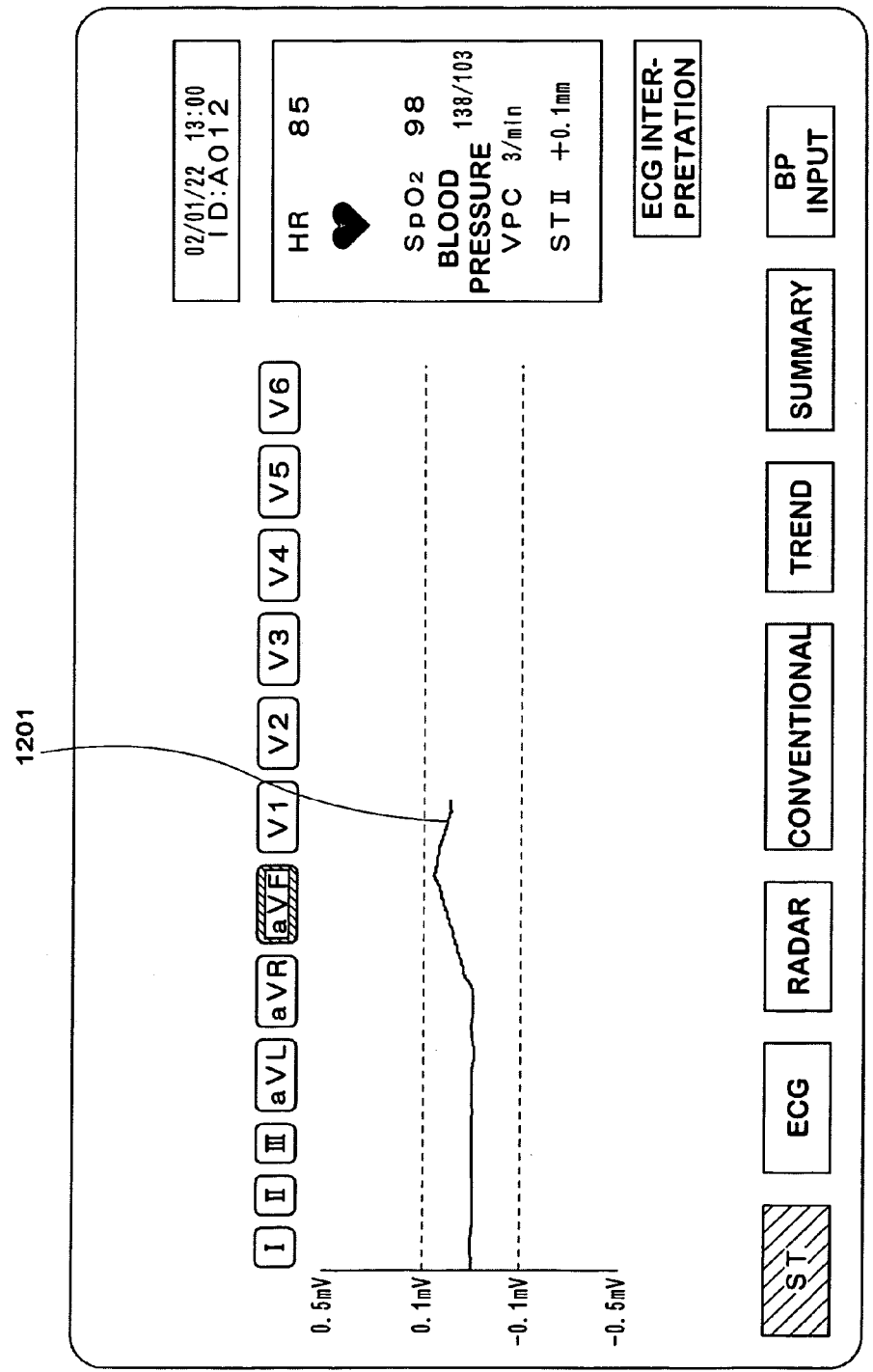
FIG. 12 illustrates a screen example of ECG data in a trend mode.

FIG. 5 illustrates a default ECG radar chart screen. Each of the default ECG radar charts are formed in the shape of a regular hexagon. When a default ECG radar chart screen such as that illustrated in FIG. 5 is displayed, the screen indicates that each identified value of the 12 leads is within a normal range. The ECG radar chart device 100 provides several modes of screen variation that are selectable in accordance with user operation. The first mode is an ECG radar chart mode as illustrated in FIG. 5 etc. The second mode is an ECG mode for displaying an ECG (refer to FIG. 11 for an ECG display). In the ECG mode, the device displays all of the ECG data from the 12 leads all at once. In alternative embodiments, the device selects one or more leads, and displays the ECG data from the selected lead(s). The third mode is a trend mode. In the trend mode, the device displays the trends of each identified value based on each of the 12 leads in a graph form. FIG. 12 illustrates a screen example for the trend mode. In FIG. 12, trend 1201 for lead aVF is displayed. For this trend, the identified values corresponding to each heart beat are displayed. In an alternative embodiment, the average of identified values over regular time intervals is displayed. On the screen, the heart rate, blood pressure value, SPO2 value, and supplementary information for ECG diagnostic, etc., are also displayed.

After step 401, the CPU 10 of the ECG radar chart device 100 processes a 12-lead ECG by use of the ECG electrodes 12 placed on the patient's body and an amplifier 13, and obtains ECG data based on the ECG. The CPU 10 stores the ECG data in memory 16 (or F-ROM 11) (step 403).

After step 403, the CPU 10 extracts identified values (which are based on the P wave, the Q wave, the R wave, the S wave, the ST segment, or the T wave) from each of the 12 ECG leads. The CPU 10 then stores the identified value data in memory 16 (or F-ROM 11) (step 405).

FIG. 16 illustrates a schematic diagram for contents of ECG data and stored identified value data. FIG. 16A illustrates examples of ECG data (which relate to lead I and lead V1), which are stored in memory 16 etc. at every ECG data sampling interval at step 403. FIG. 16B illustrates examples of identified value data (which relate to ST level and RR interval), which are stored in memory 16 etc. at every heart beat.

The CPU 10 determines whether at least one identified value extracted at step 405 shows an abnormal level (step 407). If there is no abnormal value, the CPU 10 determines whether the ECG measurement was completed (step 427). If the ECG measurement was not completed, the CPU 10 returns to step 403 and repeats the process. At the determination process at step 427, the CPU 10 utilizes an end of ECG measurement information inputting process in accordance with a user's operation, or the like.

On the other hand, at step 407, if there is an abnormal value, the CPU 10 determines the extent of the abnormality (step 409). In this case, the determination of the presence of an abnormal value can be executed by the CPU 10 to judge whether each identified value is within a normal range or not. More specifically, for example, the CPU 10 determines an abnormal value when detecting more than 0.1 mV of ST level elevation, T wave loss, or the like. In an alternative embodiment, the CPU 10 determines an abnormal value by use of the identified values from past to present (e.g. Has there been more than 0.1 mV of ST level elevation for at least 1 minute?, etc.). In that case, the CPU 10 accesses the identified values stored in memory 16. For other embodiments, abnormal values can be determined by using the magnitude of the difference between the identified values and normal values, or the difference between the identified value and an average identified value for the patient. Another identified value (e.g. PR interval etc.) instead of the identified value (which are based on a P wave, a Q wave, an R wave, a S wave, a ST segment, or a T wave) extracted at step 405 can be utilized for the abnormal value determination process executed by the CPU 10 at step 407.

When an ECG waveform contains abnormal noise due to patient movement during the ECG measurement process, it is usually difficult to extract the identified values accurately from the ECG at step 405 in FIG. 4. For example, the technology disclosed in Japanese Patent Laid-Open No. Hei 6-261871 can be utilized to obtain identified value data accurately by reducing such noise.

The CPU 10 determines which lead relates to an identified value showing an abnormal level (step 411), and chooses a radar chart for displaying the abnormal value. For example, if the lead aVR relates to an abnormal value, the CPU 10 chooses radar chart Hexa 1 to display the abnormal value (step 413) (positions for Hexa "X" is illustrated in FIG. 5). Similarly, the CPU 10 chooses the following radar charts: radar chart Hexa 2 when lead I or aVL relates to an abnormal value (step 415); radar chart Hexa 3 when lead V1 or V2 relates to an abnormal value (step 417); radar chart Hexa 4 when lead V3 or V4 relates to an abnormal value (step 419); radar chart Hexa 5 when lead V5 or V6 relates to an abnormal value (step 421); radar chart Hexa 6 when lead II, III, or aVF relates to an abnormal value (step 423). To determine the display subject at step 423, the CPU 10 adds position data indicating an identified value display position (i.e. position for displaying subject Hexa "X" and position for the radar chart point) to data indicating each identified value extracted at step 405 (i.e. identified value data). In an alternative embodiment, the CPU 10 utilizes table data that correlates the data indicating each identified value with position data indicating the display position for the identified value.

After determining the display subject for the abnormal value, the CPU 10 stores ECG radar chart data (i.e. screen display data) in memory 16 (or F-ROM 11). The ECG radar chart data is used to display a radar point with a modified level, which relates to the abnormal value, on the display subject radar chart (Hexa "X"). The CPU 10 then displays the level-modified ECG radar chart (step 425). As an explanation of processing at step 425, FIG. 6 illustrates an ECG radar chart for a case in which the CPU determines there is an abnormal value. The CPU 10 determines that the R potential and RR interval as identified values of lead I or aVL are abnormal values, and displays the radar chart Hexa 2 as illustrated in FIG. 6. At each point of the R potential and RR interval, as the point moves toward the center of hexagonal radar, the screen indicates that the extent of deviation from a normal value is increased (i.e. the extent of abnormality is much larger).

After step 425, the CPU 10 determines whether the ECG measurement was completed (step 427). If the ECG measurement was not completed, the CPU 10 returns to step 403 and repeats the processing. On the other hand, if the ECG measurement was completed, the CPU 10 completes its tasks.

As mentioned above, the ECG radar chart device 100 displays the ECG radar chart based on the patient's ECG data. Therefore, the user of the device can intuitively and easily carry out interpretation of the ECG. Also as mentioned above, one feature of the embodiment is that the device displays a radar chart as an indicator of the portion of the heart corresponding to each lead. Another feature of the embodiment is that each vertex on the radar chart corresponds to an identified value. The above-mentioned selection of lead, selection of portion of the heart, or selection of identified value for the radar chart generation, and correlation with this information are described for illustrative purposes, and therefore, can be modified by those skilled in the art.

5. Advantages of the Embodiments

In the embodiment, the CPU 10 of the ECG radar chart device 100 displays the identified ECG value obtained from the 12 leads by placing the value so that the value acts as an indicator for the portion of the heart corresponding to each lead (refer to FIG. 2 and FIG. 5). More specifically, in terms of each of the hexagonal radar charts on display 15, the (I, aVL) radar chart acts as an indicator for the front-side wall of left ventricle and higher side wall, the (V3, V4) radar chart acts as an indicator for front wall of left ventricle, the (V5, V6) radar chart acts as an indicator for side wall of left ventricle, the (II, III, aVF) radar chart acts as an indicator for the whole lower heart portion (e.g. lower wall diaphragm surface), the (V1, V2) radar chart acts as an indicator for the right ventricle, and the (aVR) radar chart acts as an indicator for the inner cavity of ventricle. Therefore, the user of the ECG radar chart device 100 can visually and intuitively understand each identified value of a patient's ECG in connection with the related portion of the heart.

In the embodiment, the CPU 10 of the ECG radar chart device 100 displays each of the hexagonal radar points on display 15 so that the each vertex acts as an indicator for each identified value (refer to FIG. 2 and FIG. 5). More specifically, each vertex of the radar chart corresponds to one of six identified values, namely: the R value (i.e. R potential or R wave height), the T value (i.e. T potential or T wave height), the Q value (i.e. Q potential or Q wave height), the ST value (i.e. ST level), the QT value (i.e. QT interval), or the RR value (i.e. RR interval). Therefore, the user of the ECG radar chart device 100 can understand the variation in the six identified values etc. simultaneously, based on the radar chart.

In the embodiment, when an identified value is normal, the CPU 10 of the ECG radar chart device 100 displays a default ECG radar chart screen (refer to step 401 in FIG. 4). On the other hand, when an identified value is abnormal, the CPU 10 determines the extent of abnormality for the value, and modifies the display subject of the radar chart corresponding to the lead that relates to the abnormal value. Therefore, the ECG radar chart device 100 can display the ECG radar chart in such a way that the device can draw the user's attention to the display when an identified value on a patient's ECG is in an abnormal range.

Figure 9:
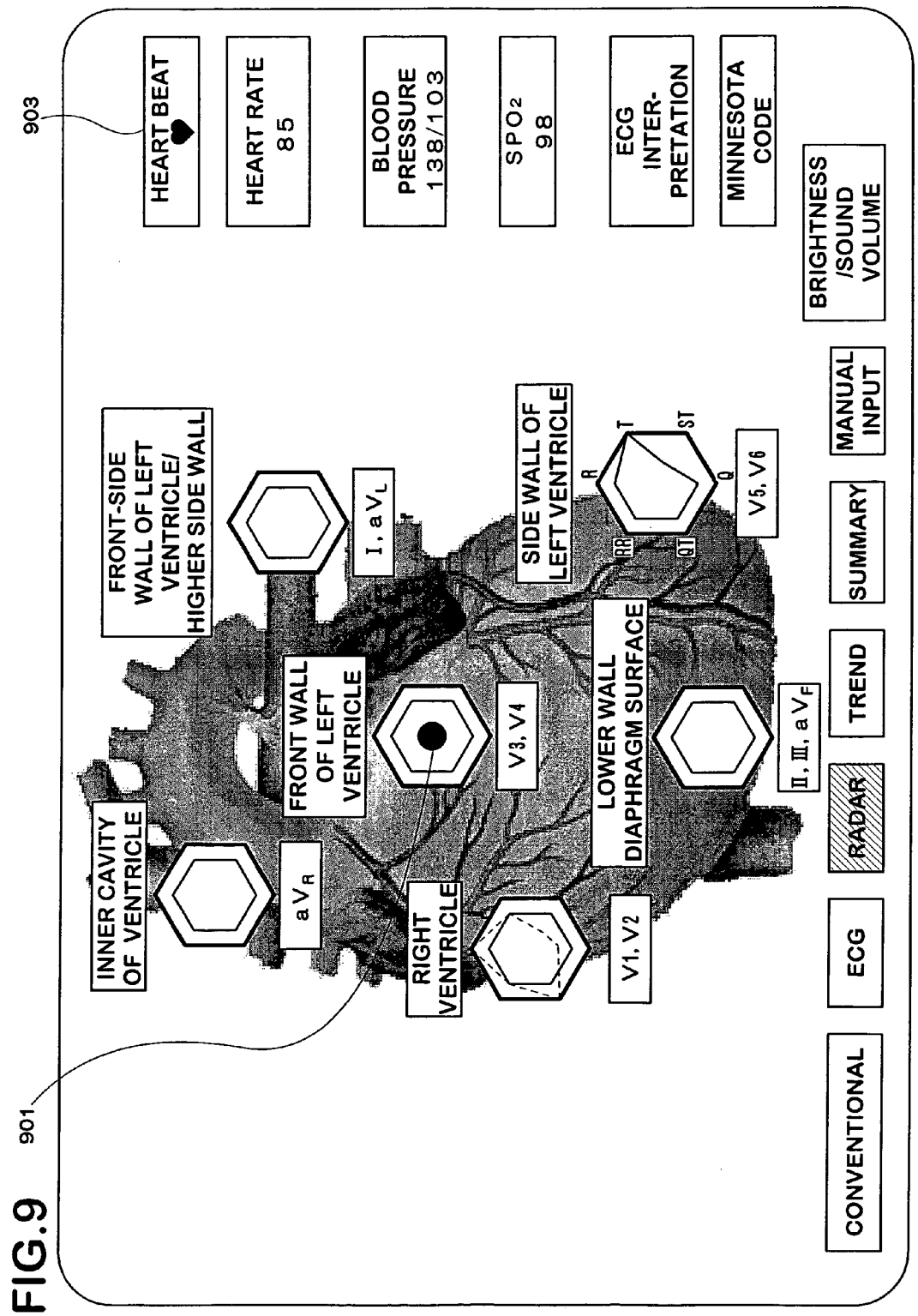
FIG. 9 illustrates a screen example of an ECG chart on a heart background.

In the embodiment, a default chart is displayed as an extension of the radar chart. The default chart display types are not limited to the above. In an alternative embodiment, a hexagonal shape is displayed inside of the radar chart as the default. Such a radar chart display is illustrated in FIG. 9. In that case, when an identified value is within a normal range, the default hexagonal shape is maintained (refer to the radar for "inner cavity of ventricle" etc., FIG. 9). On the other hand, when an identified value is in an abnormal range, for example, when an identified value exceeds the upper limit of the normal value, the level of each identified value is moved toward the extensional position of the radar chart. When an identified value falls below the lower limit of the normal value, the level of each identified value is moved toward the center of the radar chart (refer to the radar chart for "side wall of left ventricle" etc. in FIG. 9). In addition, as an alternative embodiment, as the point departs from a default position, the screen indicates that the extent of the abnormality for the identified value indicated by the point is increased.

The method for drawing the user's attention to an abnormal value is not limited to the above. The following techniques are also applicable to draw the user's attention to the value.

The first technique for drawing the user's attention to an abnormal value is to display a radar chart that varies according to the time-variation of the identified value continuously in either of the two cases, in which the value is normal or abnormal. In addition, when the value is abnormal, the first technique is to change the color of the radar chart corresponding to the abnormal value. In that case, the position of each point on the radar chart is varied continuously, even when the value is within a normal range. Regardless of the variation, the user can easily recognize that there is an abnormal value because the color of the radar corresponding to the abnormal value is changed. The color change can be executed, for example, by the following method: The device displays a radar chart in black color etc. when an identified value is normal. If the identified value becomes abnormal, the device changes the radar chart to red color etc., or displays an additional red color mark (or another color mark) inside of the radar chart (refer to the abnormal value mark 901 in FIG. 9) or around the radar chart.

The second technique for drawing the user's attention to an abnormal value is to display only a selected radar chart that corresponds to the lead relating to the abnormal value while the value remains abnormal. More specifically, upon determining that there is an abnormal value, the CPU 10 displays only the radar chart that relates to the abnormal value on the display 15 (refer to Hexa 2 in FIG. 6). In this case, it is desirable that the device displays the name of the related portion of the heart, such as "front-side wall of left ventricle" etc., in the vicinity of the radar chart so that the user can understand which portion of the heart the abnormal value relates to.

The above-mentioned features are included as advantages of the embodiments. The reason for including the above-mentioned advantages is that the embodiments adopt a unique display method. More specifically, based on an ECG that includes a wide variety of information from several leads and several identified values, the device displays the necessary information to aid in determining heart diseases in an easily and intuitively recognizable form by utilizing ECG radar charts.

6. Other Functions of the ECG Radar Chart Device

In addition to the above-mentioned ECG radar chart generating process, examples of optional functions of the ECG radar chart device 100 will be described below.

6-1. Display of Heart Beat Condition

The ECG radar chart device 100 displays a specific flashing symbol (or mark) in order to show a heart beat condition (heart beat related information) (which corresponds to "varying display style"). More specifically, the CPU 10 processes a display of the flashing heart mark 903 according to the heart rhythm measured, as illustrated in FIG. 9.

The user can confirm that the ECG radar chart device 100 is running normally, and can also check the patient's heart beat condition. In an alternative embodiment, the device outputs a specific sound (e.g. bleep sound) from the speaker 17 according to the heart rhythm, in conjunction with the flashing mark or instead of the flashing mark.

6-2. Display of Measurement History During ECG Measurement

During the ECG radar chart generation process, the ECG radar chart device 100 can optionally display historical data of the patient's identified value levels (history of the feature value analysis results). More specifically, the CPU 10 can display the history of an identified value level that is in an abnormal range by dotted lines, such as on the radar chart of "right ventricle" illustrated in FIG. 9.

The user can ascertain that a patient may have a particular type of heart disease by checking the history of the identified value level. In an alternative embodiment of the display of identified value level history, any chart tracks instead of dotted lines can be applied to display the history. For example, the device can display the tracks in a different color from that being used for the ongoing identified value level. In another alternative embodiment, the device can display an additional specific mark next to a radar chart, corresponding to a lead relating to a determined abnormal value. In another alternative embodiment, instead of displaying all of the abnormal value history, the device can display the history only when the number of times a determined value becomes abnormal exceeds a certain threshold number (e.g. when the number of times a determined value becomes abnormal exceeds three times).

6-3. Display of History Summary after ECG Measurement

The ECG radar chart device 100 displays a history summary of the identified value levels (history summary of the feature value analysis results) after completing the ECG measurement. The CPU 10 displays the history by utilizing the identified value data stored in memory 16 (or F-ROM 11). More specifically, the CPU 10 can optionally display a time-varied ECG radar charts in fast-forward on display 15 after completing the ECG measurement in accordance with user operation. The history can be represented by playing the screen illustrated in FIG. 6 in a frame advance (simplified moving picture playback).

The doctor in a hospital to which a patient is transferred can promptly understand the general trends for the patient's identified value level history. The function of the fast-forward playing of the identified value can be executed by extracting and displaying abnormal values only. In order to display the "history summary of the feature value analysis results," the device can display all the radar charts that correspond to the abnormal values determined as freeze-frame pictures rather than by fast-forward playing.

6-4. Warning for Impracticable Analysis

The ECG radar chart device 100 displays a certain warning (warning signal) during ECG radar chart generating process when an ECG electrode 12 is detached from the patient or when trouble occurs in display processing (a condition in which the analysis can not be executed), or the like. More specifically, the CPU 10 displays a warning message stating "electrode detached" etc., on display 15.

The user who sees the warning can promptly understand that the ECG radar chart generating process has been interrupted by the trouble. In alternative embodiments, in order to draw the user's attention to the display, the CPU 10 changes the color of the whole display or the color of part of the display, or outputs a warning sound (e.g. an alarm sound).

7. Other Embodiments

7-1. Application Embodiments of ECG Radar Chart Device

In the embodiments, the ECG radar chart device 100 is used in emergency medical arenas such as in ambulances or in hospitals. In alternative embodiments, the device can be used in any emergency medical arena in a portable form, or used for home medical care by setting the device in a home. Devices that have similar functions with that of the ECG radar chart device 100 can be installed in the driver's seat of an automobile or an electric train, an airplane cockpit, or the like, in order to prevent a serious accident from occurring when the driver develops a heart attack due to myocardial infarction etc. In other embodiments, such devices can be installed on a toilet seat, etc., for daily health care. For those applications, it is advantageous for the ECG electrodes 12 to be installed in an area with which the subject's body necessarily makes contact, such as a handle, toilet seat, handrail, or the like.

7-2. Embodiments of Device Configuration

In the embodiments, the ECG radar chart device 100 executes both ECG measurement and ECG radar chart display. In alternative embodiments, those functions can be separately executed by two or more discrete devices. For example, one device can execute an ECG measurement and ECG data output, and the other device can execute an ECG radar chart display based on the ECG data input. An example of a system adopting such a device configuration will be described below together with FIG. 8.

7-3. Embodiments of ECG Radar Chart System

FIG. 8 illustrates the ECG radar chart system as another embodiment of the present invention. The ECG radar chart system includes ambulance 70, in which ECG radar chart sending device 700 is installed, control center 80, in which ECG radar chart receiving device 800 is installed, A-hospital 74, and B-hospital 76, in which a personal computer (which will be described as "B-hospital PC 750") is installed. The system enables the control center to promptly determine which hospital a patient should be transferred to by utilizing an ECG radar chart.

An overview of the system processing will be described together with FIG. 8. The CPU of the ECG radar chart sending device 700 runs an ECG on a patient (step 1). The CPU sends ECG data and identified value data to the ECG radar chart receiving device 800 (step 2). The CPU of the ECG radar chart receiving device 800 receives the ECG data and identified value data, and stores them (step 3). The CPU of device 800 generates and displays an ECG radar chart (step 4). The user (e.g. the doctor) of ECG radar chart receiving device 800 checks whether the ECG radar chart shows an abnormal value or not (refer to FIG. 6). The user evaluates the patient's heart disease, and determines a hospital to which the patient should be transferred (step 5). The CPU of the ECG radar chart receiving device 800 sends ECG data, identified value data, and ECG radar chart data to B-hospital PC 750 at the hospital determined (e.g. B-hospital 76) (step 6). The CPU of the radar chart receiving device 800 sends the name of the hospital determined, the hospital location, etc. to ECG radar chart sending device 700 (step 7). As mentioned above, since the ECG radar chart enables the user to utilize it as an intuitive aid in ECG interpretation, while still in the emergency medical situation the user can promptly determine to which hospital the patient should be transferred.

Figure 14:
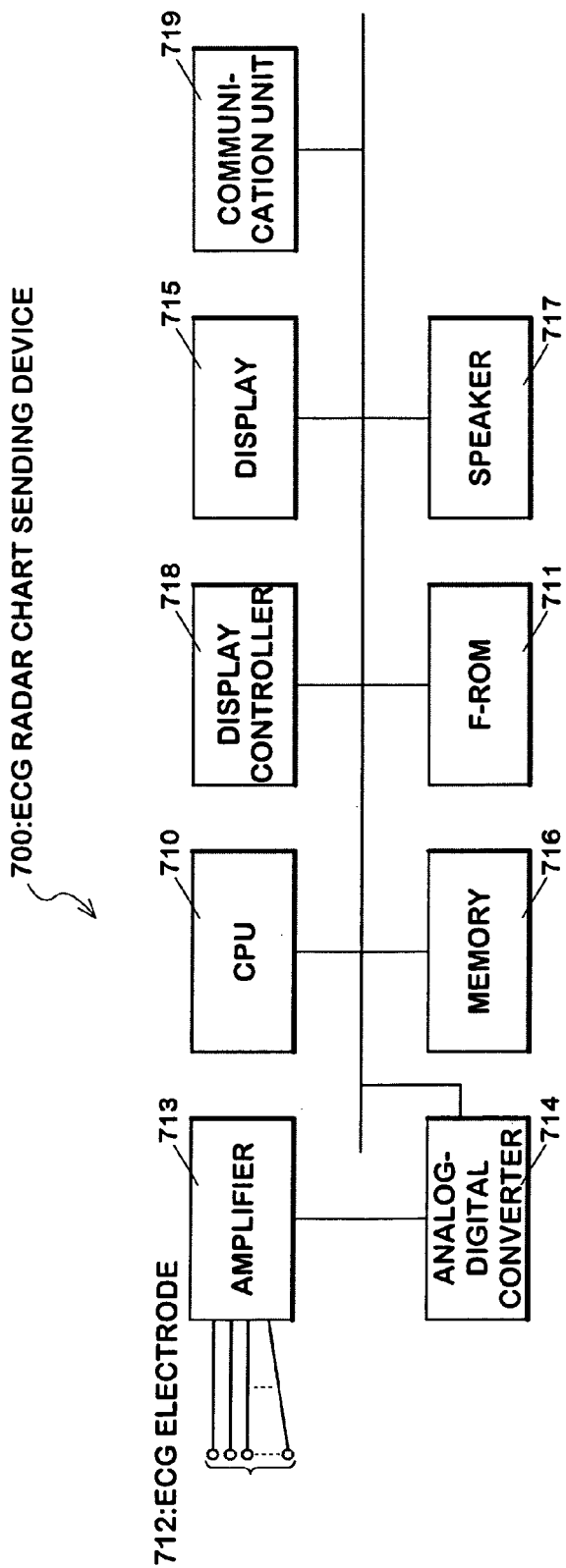
FIG. 14 illustrates a hardware configuration example for an ECG radar chart sending device.

FIG. 14 illustrates a hardware configuration example of the ECG radar chart sending device 700 by use of a CPU. The ECG radar chart sending device 700 includes ECG electrodes 712, amplifier 713, analog-digital converter 714, CPU 710, Flash-ROM 711, memory 716, display controller 718, display 715, speaker 717, and communication unit 719 for communicating with the ECG radar chart receiving device 800 or the like.

Figure 15:
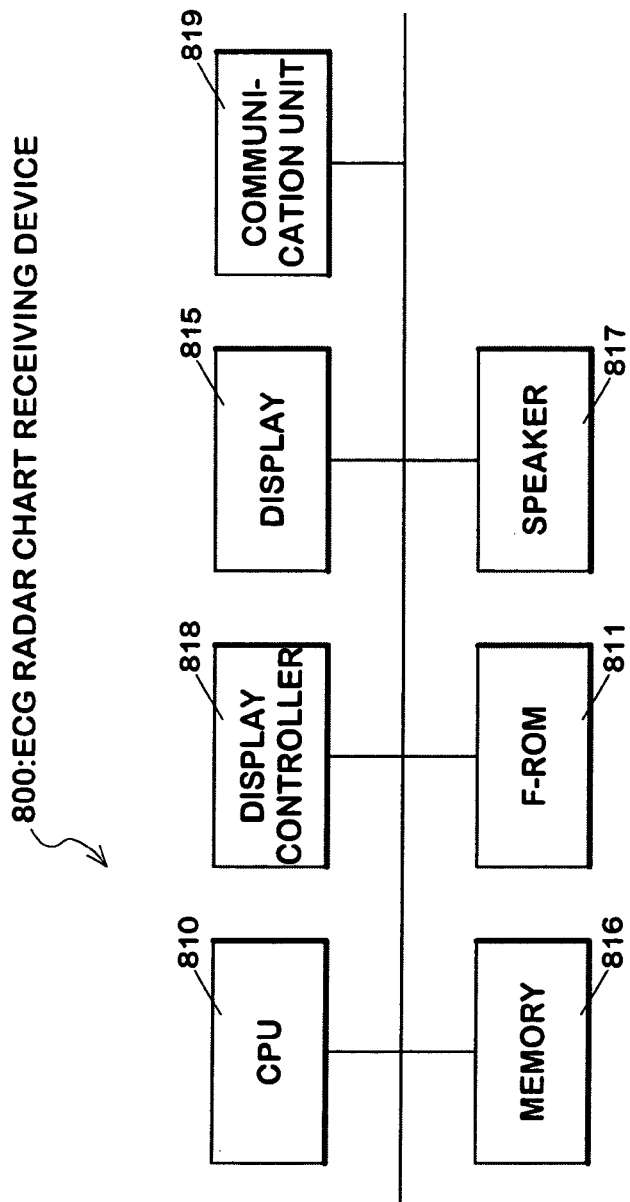
FIG. 15 illustrates a hardware configuration example for an ECG radar chart receiving device.

FIG. 15 illustrates a hardware configuration example of the ECG radar chart receiving device 800 by use of a CPU. The ECG radar chart receiving device 800 includes CPU 810, Flash-ROM 811, memory 816, display controller 818, display 815, speaker 817, and communication unit 819 for communicating with the ECG radar chart sending device 700 or the like. A hardware configuration of the B-hospital PC 750 is similar to that of the ECG radar chart receiving device 800. The functions of the hardware component illustrated in FIG. 14 and FIG. 15 are similar to those of the hardware illustrated in FIG. 3.

Communication links between device 700, device 800, and PC 750 can include LAN, Ethernet™, telephone lines, wireless communication, the Internet, wire communication, infrared data communication, mobile phone, Bluetooth, PHS, or the like.

A program flowchart for data transmission and reception processing by the ECG radar chart system will be described below together with FIG. 13.

Figure 13:
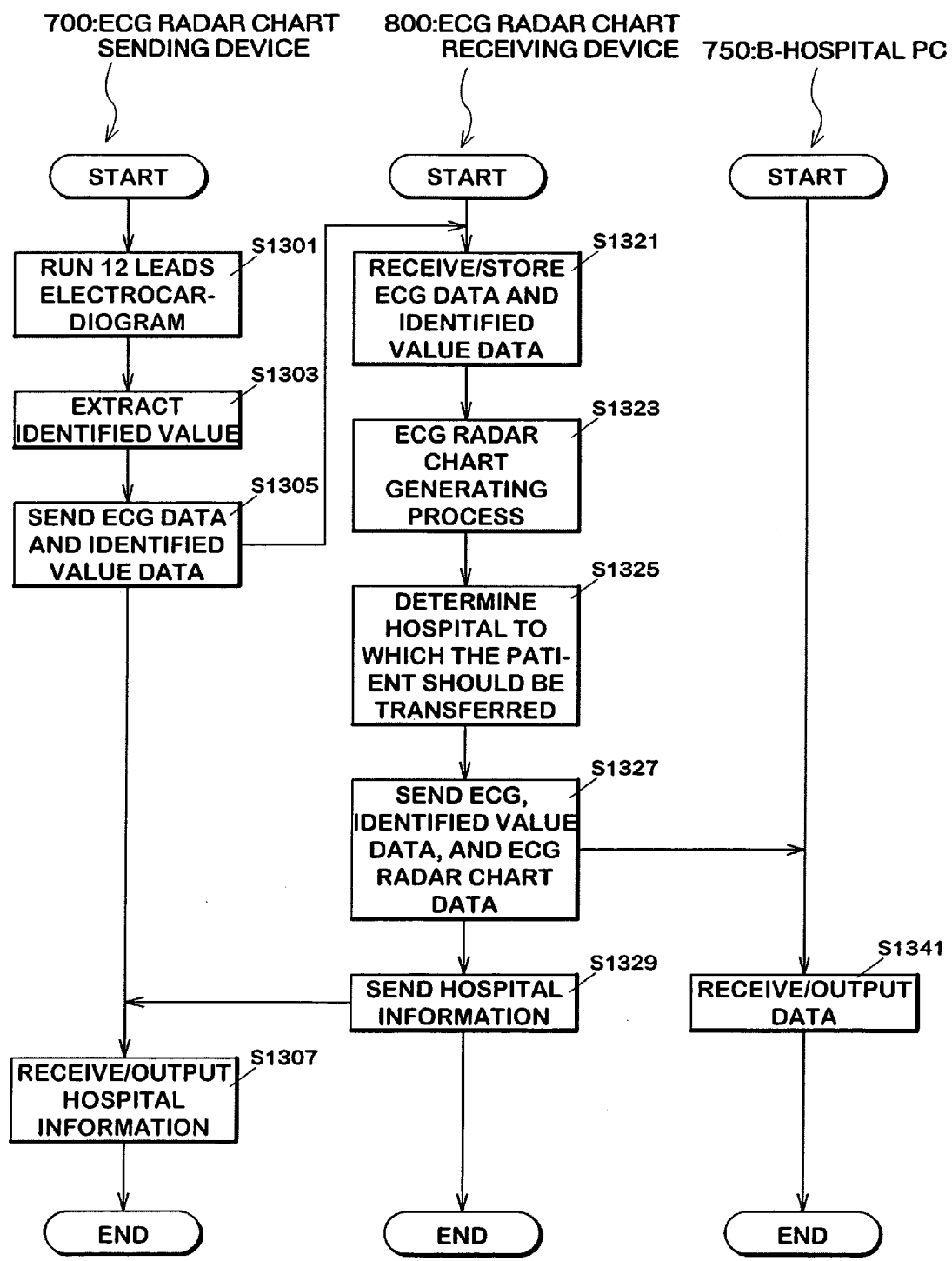
FIG. 13 illustrates a program flowchart for data transmission and reception processing of the ECG radar chart system.

The CPU 710 of the ECG radar chart sending device 700 runs ECG data from 12 ECG leads, and stores ECG data as results of the ECG measurement in memory 716 (or F-ROM 711) (step 1301 in FIG. 13). The CPU 710 extracts identified values from each of the 12 ECG leads, and stores the identified value data in memory 716 (or F-ROM 711) (step 1303). The CPU 710 sends the ECG data and identified value data (step 1305).

The CPU 810 of the ECG radar chart receiving device 800 receives the ECG data and identified value data, and stores them in memory 816 (or F-ROM 811) (step 1321). The CPU 810 executes ECG radar chart generating process (step 1323). The ECG radar chart generating process executed is similar to the processes in step 407 to step 425 in FIG. 4.

The user (e.g. the doctor) of the ECG radar chart receiving device 800 checks whether the ECG radar chart displayed as the processing result of step 1323 shows an abnormal value or not (refer to FIG. 6). The user evaluates the patient's heart disease, and determines to which hospital the patient should be transferred, based on the ECG radar chart. The user inputs the determination results in the device 800. The CPU 810 obtains the determination information etc. of the hospital (step 1325).

The CPU 810 sends the ECG data, the identified value data, and ECG radar chart data (step 1327). The CPU of B-hospital PC 750 receives those data, and outputs them to a display etc. (step 1341). The CPU 810 sends the determination information about the hospital, etc., to the ECG radar chart sending device 700 (step 1329). The CPU 710 of ECG radar chart sending device 700 receives the determination information about the hospital etc., and outputs them to a display 715, etc. (step 1307).

As mentioned above, the ECG radar chart receiving device 800 receives the ECG data and identified value data. In an alternative embodiment, the device receives data (i.e. ECG radar chart data) that is to display radar charts based on the ECG data (the data received corresponds to the term "chart data that is to display a chart that relates the feature value to each portion of the heart"). In communications between the ECG radar chart sending device 700 and the ECG radar chart receiving device 800, the ECG data and/or identified value data and the ECG radar chart data can be subjects for data transmission and reception. In that case, the CPU 710 of the ECG radar chart sending device 700 executes the ECG radar chart generation process of step 1323. When the configuration of that device is applied, the ECG radar chart receiving device 800 corresponds to the term "ECG chart-display device", and the device 800 includes "means for receiving," "means for displaying," and "means for displaying the abnormal value."

In communications between the ECG radar chart receiving device 800 and B-hospital PC 750, subjects for data transmission and reception can be any of the ECG data, identified value data, or ECG radar chart data.

7-4. Embodiments of ECG Radar Chart Display

In the embodiments, the CPU 10 of the ECG radar chart device 100 displays the ECG radar chart based on the ECG data (refer to FIG. 2 or FIG. 5). As alternative embodiments for chart display based on the ECG data, display methods such as those illustrated in FIG. 7 are applied. An overview of each display method will be given.

Figure 7A:
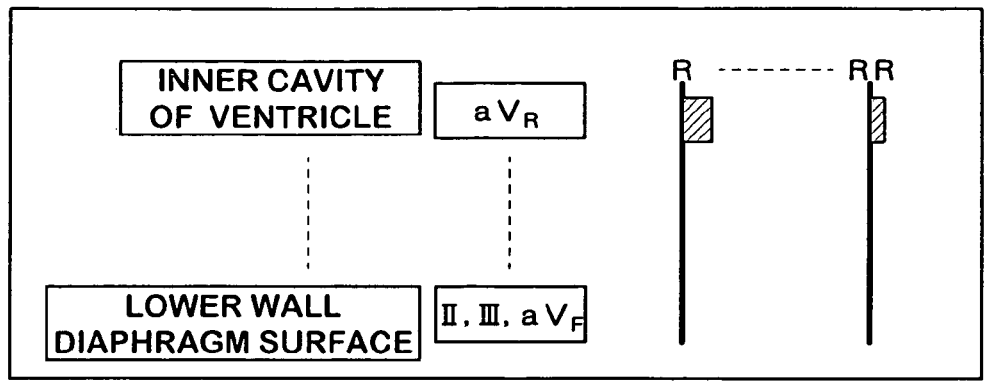
FIGS. 7A, 7B, and 7C illustrate other examples of an ECG chart.

FIG. 7A illustrates a screen in which ECG data are displayed in a bar graph form. As illustrated in FIG. 7A, varying appearances of the R potential and the RR interval as identified values are displayed, and the values correspond to the lead "aVR," relating to the condition of inner cavity of ventricle.

Figure 7B:
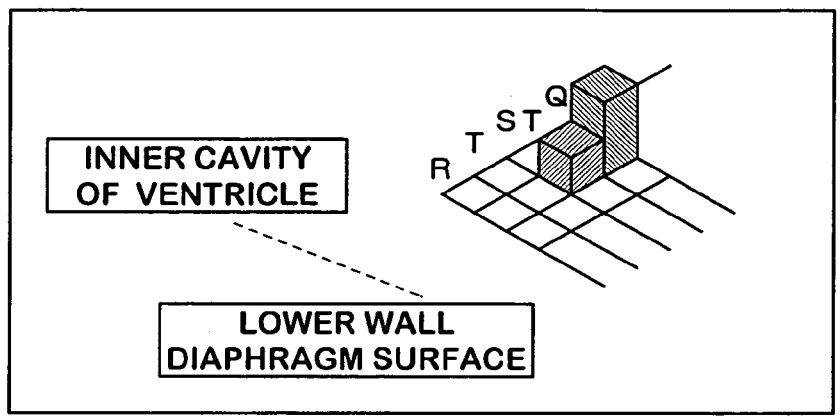

FIG. 7B illustrates a screen in which the ECG data are displayed in a three dimension graph form. As illustrated in FIG. 7B, varying appearances of the ST level and the Q potential are displayed, and the values correspond to the lead "aVR," relating to the conditions of inner cavity of ventricle.

Figure 7C:
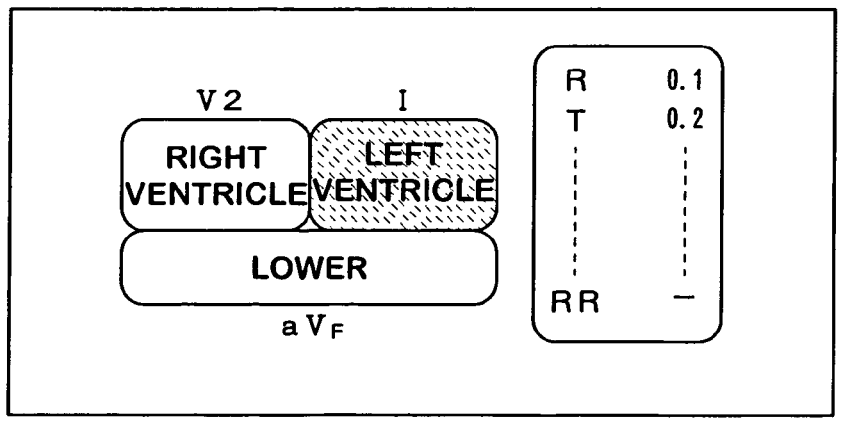

FIG. 7C illustrates a screen in which the ECG data are displayed on a heart diagram, with a listing of identified values provided. As illustrated in FIG. 7C, the identified values (i.e. R potential and T potential) are displayed as the determined abnormal values, and the values correspond to the lead "I" relating to conditions of left ventricle.

In any of the display method as mentioned above, it is desirable that the device displays each identified value with an indication corresponding to the related portion of the heart as illustrated in FIG. 2 or FIG. 7, so that the user of the device can promptly understand necessary information that should be interpreted from the ECG waveforms.

In the embodiments, the ECG radar chart is displayed on the display 15. In an alternative embodiment, a print-out hard copy that indicates an ECG radar chart (which corresponds to the term "ECG chart displayed object") can be utilized in the medical fields etc.

Figure 10:
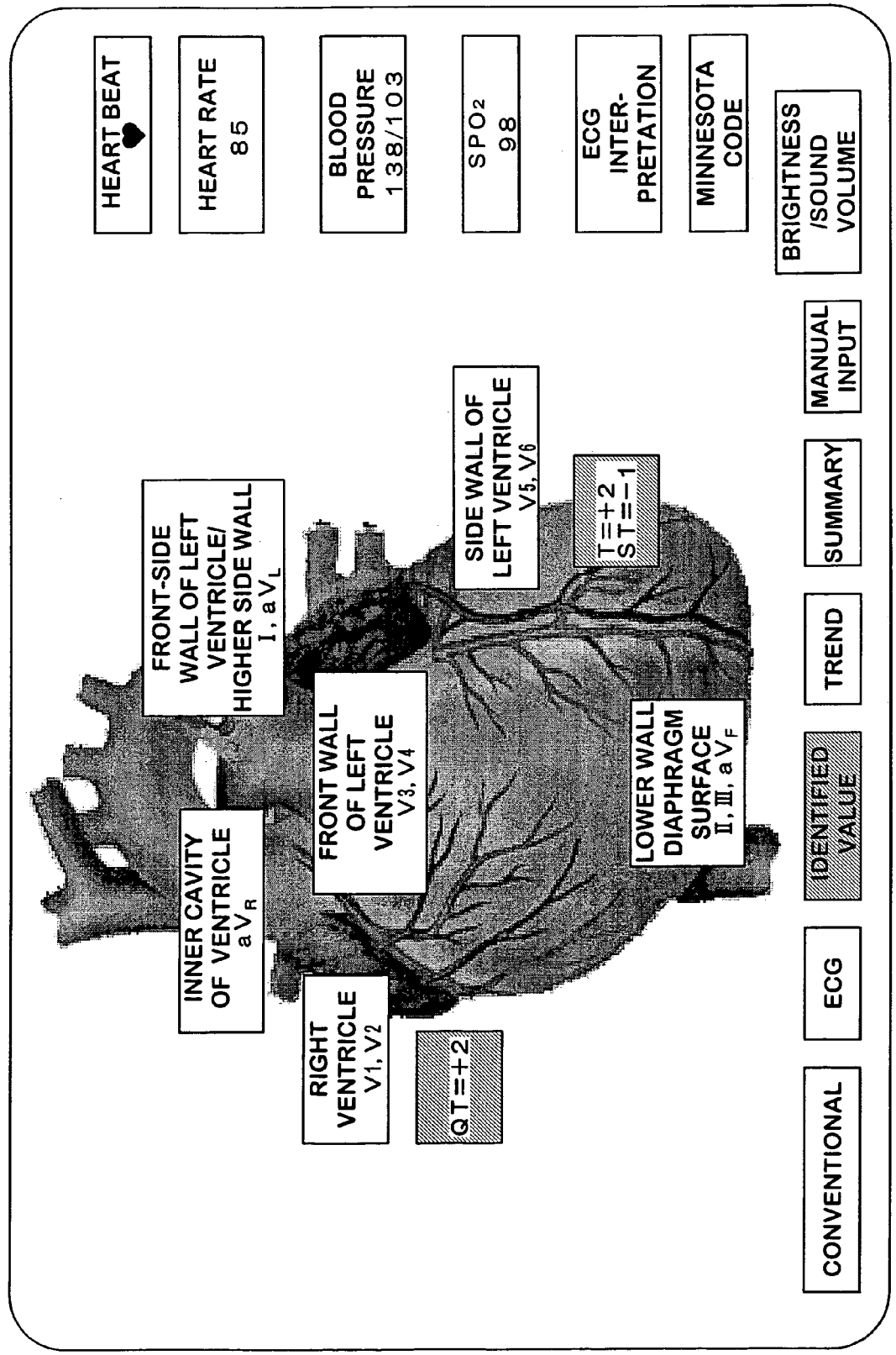
FIG. 10 illustrates a screen example of ECG data on a heart background.

7-5. Embodiments of Identified Value Display Corresponding to a Heart Background Image FIG. 9 and FIG. 10 illustrate modified embodiments of the ECG data display. In those embodiments, the ECG data are displayed on a screen with a heart image background (i.e. background picture) as a "heart image," and that display corresponds to the terms "display a chart that relates the feature value to each portion of the heart," "display the chart that arranges each feature value at the corresponding portion of the heart," or "display the feature value on a heart image".

As illustrated in FIG. 9, the CPU 10 of the ECG radar chart device 100 displays a radar chart on a heart background (which corresponds to the term "heart image"). More specifically, each of the radar charts is displayed over a background picture that indicates a typical heart shape. Furthermore, each of the radar charts is placed on a portion of the heart to which the radar chart corresponds. It is desirable that the heart background includes identifiable indications for each specific portion of the heart such as "inner cavity of ventricle" or "right ventricle," as illustrated in FIG. 9. In alternative embodiments, the heart background includes brief portion descriptions such as heart left portion, right portion, or the like, rather than the specific portion names as illustrated in FIG. 9.

As illustrated in FIG. 10, the CPU of the "ECG display device" displays identified values on a heart background image. More specifically, each of the identified values obtained by the CPU (which corresponds to "means for obtaining feature value data") is displayed over the background picture that indicates the heart shape, as in FIG. 9. Furthermore, the CPU (which corresponds to the term "means for displaying the feature value") places each identified value on the portion of the heart to which the identified value corresponds. As illustrated in FIG. 10, the device displays only abnormal levels of identified value(s) that were determined as abnormal values. The abnormal level represents the extent of abnormality as +1, +2, . . . etc., when the value exceeds the upper limit of a normal value, or −1, −2, . . . etc., when the value falls below the lower limit of a normal value. In alternative embodiments, the device displays all of the identified value levels, or displays absolute values of the identified values.

In another embodiment, upon determining that an identified value is an abnormal value, the device modifies the color of the portion of the heart to which the identified value corresponds. More specifically, when the identified value relating to the right ventricle is an abnormal value, the device displays a flashing red color at the right ventricle portion on the heart background image. In that case, the term "means for display control" in the claims corresponds to means for displaying a warning at a heart portion corresponding to a feature value on a heart image when the feature value is in an abnormal range.

The above-mentioned display methods make it possible for the user to intuitively understand which portion of the heart relates to the identified values observed.

7-6. Program Execution

In the embodiments, the computer program for the CPU 10 is stored in the F-ROM 11. The computer program can be installed on the hard disk etc. from an installation CD-ROM (not shown). In alternative embodiments, the program can be installed from computer-readable storage media such a flexible disk (FD) or IC card (not shown). Alternatively, the program can be downloaded to the devices via the communications lines. The program can also be installed on the devices from the CD-ROM, and the device executes the installed program. In alternative embodiments, the device can directly execute the program stored on the CD-ROM.

Computer-executable programs used in the embodiments include a program to be executable just after installation, a program that needs to be converted to another format (e.g. decompressing compressed data), or a program to be executable within a module.

A general description of the present invention as well as preferred embodiments of the invention has been set forth above. It is to be expressly understood, however, that the terms described above are for purpose of illustration only and are not intended as definitions of the limits of the invention. Those skilled in the art to which the present invention pertains will recognize and be able to practice other variations in the system, device, and methods described which fall within the teachings of this invention. Accordingly, all such modifications are deemed to be within the scope of the invention.

What is claimed is:

1. An electrocardiogram (ECG) chart data-generating device for generating radar chart data to be used to display radar charts based on measured ECG data, comprising:
   means for generating feature value data indicating ECG feature values of grouped ECG data, said grouped ECG data being obtained by grouping the ECG data according to each physical location of the heart, and
   means for generating chart data corresponding to each physical location of the heart, wherein the chart data is used to display a radar chart which shows feature values of each group represented by the feature value data, said feature value being displayed such that said feature value displayed is correlated with the corresponding physical location of the heart from which the feature value is measured.

2. The device according to claim 1, further comprising:
   means for varying the display style of the feature value when the feature value is in an abnormal range.

3. The device according to claim 2, wherein the means for varying the display style is to hold display of the feature value constant even when the feature value varies within a normal range.

4. The device according to claim 1, wherein the chart data is displayed in the radar chart that correlates to each portion of the heart including at least left portion of the heart, right portion of the heart, bottom portion of the heart, front portion of the heart, or inner portion of the heart.

5. The device according to claim 1, wherein the feature value data is based on the constituent elements of an ECG including at least P wave, Q wave, R wave, S wave, ST segment, or T wave.

6. The device as in one of claim 1, wherein the chart data is displayed in the feature value on a heart image.

7. A non-transitory computer readable medium having stored thereon a computer program for an ECG chart data-generating device that generates chart data to be used to display charts based on measured ECG data, wherein the program is implemented in a computer and capable of causing the computer to perform:
   generating feature value data indicating ECG feature values of grouped ECG data, said grouped ECG data being obtained by grouping the ECG data according to each physical location of the heart, and
   generating chart data corresponding to each physical location of the heart, wherein the chart data is to be used to display a radar chart which shows feature values of each group represented by the feature value data, said feature value being displayed such that said feature value displayed is correlated with the corresponding physical location of the heart from which the feature value is measured.

8. An ECG chart data-generating device for generating radar chart data based on measured ECG data comprising:
- a central processing unit (CPU) of the ECG chart data-generating device adapted to generate feature value data indicating ECG feature values of grouped ECG data, said grouped ECG data being obtained by grouping the ECG data according to each physical location of the heart, and
- wherein the CPU generates the radar chart data corresponding to each physical location of the heart, wherein the chart data is used to display a radar chart which shows feature values of each group represented by the feature value data, said radar chart being displayed such that said radar chart displayed is correlated with the corresponding physical location of the heart from which the feature values of the radar chart is measured.

* * * * *